(12) United States Patent
Hasegawa et al.

(10) Patent No.: US 11,144,771 B2
(45) Date of Patent: Oct. 12, 2021

(54) IN-VEHICLE DEVICE, CONTROL METHOD, PROGRAM, AND VEHICLE

(71) Applicant: TOYOTA JIDOSHA KABUSHIKI KAISHA, Toyota (JP)

(72) Inventors: Hideo Hasegawa, Nagoya (JP); Keiko Kameda, Toyota (JP); Misa Ejiri, Nagoya (JP); Shintaro Naruse, Nisshin (JP); Tadahiro Kashiwai, Nagoya (JP); Naoya Oka, Toyota (JP); Kensuke Koike, Nisshin (JP); Hiroyuki Monji, Nagoya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 0 days.

(21) Appl. No.: 16/690,242

(22) Filed: Nov. 21, 2019

(65) Prior Publication Data

US 2020/0210734 A1 Jul. 2, 2020

(30) Foreign Application Priority Data

Dec. 26, 2018 (JP) .............................. JP2018-243357

(51) Int. Cl.
| | |
|---|---|
| *H04N 7/18* | (2006.01) |
| *G06K 9/00* | (2006.01) |
| *G06Q 20/32* | (2012.01) |
| *G06N 20/00* | (2019.01) |
| *G01C 21/34* | (2006.01) |
| *G16H 10/65* | (2018.01) |

(52) U.S. Cl.
CPC ..... *G06K 9/00845* (2013.01); *G01C 21/3438* (2013.01); *G06N 20/00* (2019.01); *G06Q 20/3223* (2013.01); *G16H 10/65* (2018.01); *G06K 2209/21* (2013.01)

(58) Field of Classification Search
CPC ........... G06K 9/00845; G06K 2209/21; G06Q 20/3223; G06N 20/00; G01C 21/3438; G16H 10/65
See application file for complete search history.

(56) References Cited

U.S. PATENT DOCUMENTS

| | | | |
|---|---|---|---|
| 10,233,021 B1* | 3/2019 | Brady | ................. G05D 1/0282 |
| 2003/0172042 A1 | 9/2003 | Agui | |
| 2018/0043901 A1* | 2/2018 | Kim | ....................... A61B 5/021 |
| 2019/0061772 A1* | 2/2019 | Prinz | ....................... A61B 5/18 |

FOREIGN PATENT DOCUMENTS

| | | |
|---|---|---|
| JP | 2003-256517 A | 9/2003 |
| JP | 2017-111506 A | 6/2017 |

* cited by examiner

*Primary Examiner* — Richard T Torrente
(74) *Attorney, Agent, or Firm* — Oblon, McClelland, Maier & Neustadt, L.L.P.

(57) ABSTRACT

An in-vehicle device includes a control unit, a storage unit configured to store features of each subject that is a person, and an image capturing unit. The control unit obtains an image captured by the image capturing unit, detects a subject in the obtained image based on the features stored in the storage unit, recognizes a behavior of the detected subject from the obtained image, and stores the detected subject and the recognized behavior in association with each other.

14 Claims, 7 Drawing Sheets

FIG. 4

| PERSON'S ID | FEATURE AMOUNT | ADDRESS |
|---|---|---|
| P01 | F01 | 1-1, B DISTRICT, A CITY |
| P02 | F02 | 1-10, B DISTRICT, A CITY |
| P03 | F03 | 3-1, C DISTRICT, A CITY |
| ⋮ | ⋮ | ⋮ |

FIG. 5

| PERSON'S ID | DATE | BEHAVIOR | MEASURED VALUE (BLOOD PRESSURE) | PURCHASED ITEM |
|---|---|---|---|---|
| P01 | DEC. 1, 2018 | WALKING WITH CANE | 100/50mmHg | - |
| P02 | DEC. 1, 2018 | LIMPING | 150/90mmHg | MEDICINE |
| ⋮ | ⋮ | ⋮ | ⋮ | ⋮ |

IN-VEHICLE DEVICE, CONTROL METHOD, PROGRAM, AND VEHICLE

INCORPORATION BY REFERENCE

The disclosure of Japanese Patent Application No. 2018-243357 filed on Dec. 26, 2018, including the specification, drawings, and abstract is incorporated herein by reference in its entirety.

BACKGROUND

1. Technical Field

The present disclosure relates to an in-vehicle device, a control method, a program, and a vehicle.

2. Description of Related Art

It is well known that a door-to-door sales vehicle sends e-mail to a communication terminal of a target (for example, a home care recipient) registered for a round service, and receives a reply message, such as "condition is good" from the communication terminal for confirming the target's safety (see, for example, Japanese Unexamined Patent Application Publication No. 2003-256517). In a case where the door-to-door sales vehicle does not receive the reply message from the communication terminal, the salesperson visits the user's house in person.

SUMMARY

However, the user has to send the reply message in this system. In principle, the salesperson visits the user's house when there is no reply, but this is very unlikely since frequent visits are quite a burden on the salesperson.

Considering the problem stated above, the present disclosure is made to provide an in-vehicle device, a control method, a program, and a vehicle, each capable of checking the daily health condition of a target without undue burden on the target.

An in-vehicle device according to one embodiment includes a control unit, a storage unit configured to store features of each subject that is a person, and an image capturing unit. The control unit obtains an image captured by the image capturing unit, detects a subject in the obtained image based on the features stored in the storage unit, recognizes a behavior of the detected subject from the obtained image, and stores the detected subject and the recognized behavior in association with each other.

A control method according to one embodiment is a control method in an in-vehicle device including a control unit, a storage unit configured to store features of each subject that is a person, and an image capturing unit. The method includes a step of obtaining an image captured by the image capturing unit, a step of detecting a subject in the obtained image based on the features stored in the storage unit, a step of recognizing a behavior of the detected subject from the obtained image, and a step of storing the detected subject and the recognized behavior in association with each other.

A program according to one embodiment is a program for an in-vehicle device including a control unit, a storage unit configured to store features of each subject that is a person, and an image capturing unit. The program causes the in-vehicle device to obtain an image captured by the image capturing unit, detect a subject in the obtained image based on the features stored in the storage unit, recognize a behavior of the detected subject from the obtained image, and store the detected subject and the recognized behavior in association with each other.

A vehicle according to one embodiment includes a control unit, a storage unit configured to store subjects that are one or more persons in association with features and an address for each of the subjects, and an image capturing unit. The control unit obtains an image captured by the image capturing unit, detects a subject in the obtained image based on the features stored in the storage unit, recognizes a behavior of the detected subject from the obtained image, and stores the detected subject and the recognized behavior in association with each other. When it is determined that at least one of one or more designated subjects has not been detected, the vehicle moves to an address of at least one undetected subject.

With an in-vehicle device, a control method, a program, and a vehicle of the present disclosure, it is possible to check the daily health condition of a target without undue burden on the target.

BRIEF DESCRIPTION OF THE DRAWINGS

Features, advantages, and technical and industrial significance of exemplary embodiments will be described below with reference to the accompanying drawings, in which like numerals denote like elements, and wherein:

FIG. 4 is a diagram illustrating a first example of data stored in a storage unit of the present embodiment;

FIG. 5 is a diagram illustrating a second example of data stored in a storage unit of the present embodiment.

DETAILED DESCRIPTION OF EMBODIMENTS

Hereinafter, embodiments will be described with reference to drawings.

Figure 1:
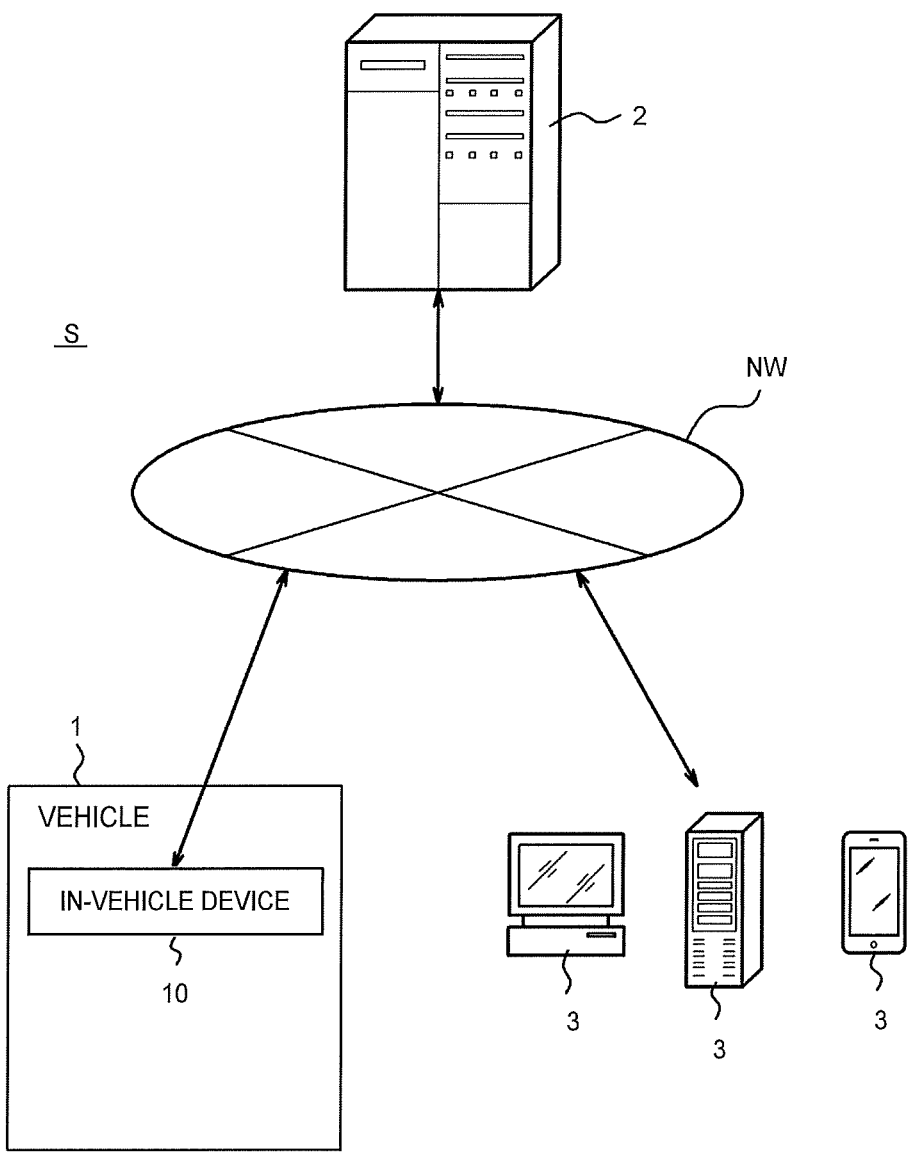
FIG. 1 is an overall view illustrating an information processing system of the present embodiment.

FIG. 1 is an overall view illustrating an information processing system S of the present embodiment. The information processing system S includes a vehicle 1, a server 2, and a user terminal 3. The vehicle 1 includes an in-vehicle device 10. The vehicle 1 of the present embodiment is, for example, an automobile, but is not limited thereto and may be any vehicle. In FIG. 1, one vehicle 1 and one server 2 are illustrated for convenience of description. However, the number of the vehicle 1 and the number of the server 2 may be one or more, respectively. The vehicle 1, the server 2, and the user terminal 3 are configured to be communicable via a network NW including, for example, a mobile communication network and the Internet.

Hereinafter, an overview of processing executed by the information processing system S of the present embodiment will be described. It is exemplified that the vehicle 1 is a door-to-door sales vehicle in the present embodiment. When the vehicle 1 arrives at a predetermined location, the vehicle 1 captures an image of its surroundings using the in-vehicle device 10 and detects a subject that is a person from the captured image while selling goods or services. The in-vehicle device 10 recognizes a behavior of the detected subject from the captured image, and stores the detected subject and the recognized behavior in association with each other. In other words, the in-vehicle device 10 recognizes the behavior of the subject by capturing the image and performing image analysis on the captured image.

As stated above, according to the present embodiment, it is possible to check the daily health condition or safety of a target (for example, an elderly person) without undue burden of operating a terminal, or the like, on the target. Further, the in-vehicle device 10 shares the obtained information with registered parties concerned (for example, a family of an elderly person, a local government, a government agency, or a family doctor), and thus it is possible to enhance monitoring, medical care, or the like, for the target.

Hereinafter, respective internal configurations of the in-vehicle device 10, the server 2, and the user terminal 3 will be described in detail.

Figure 2A:
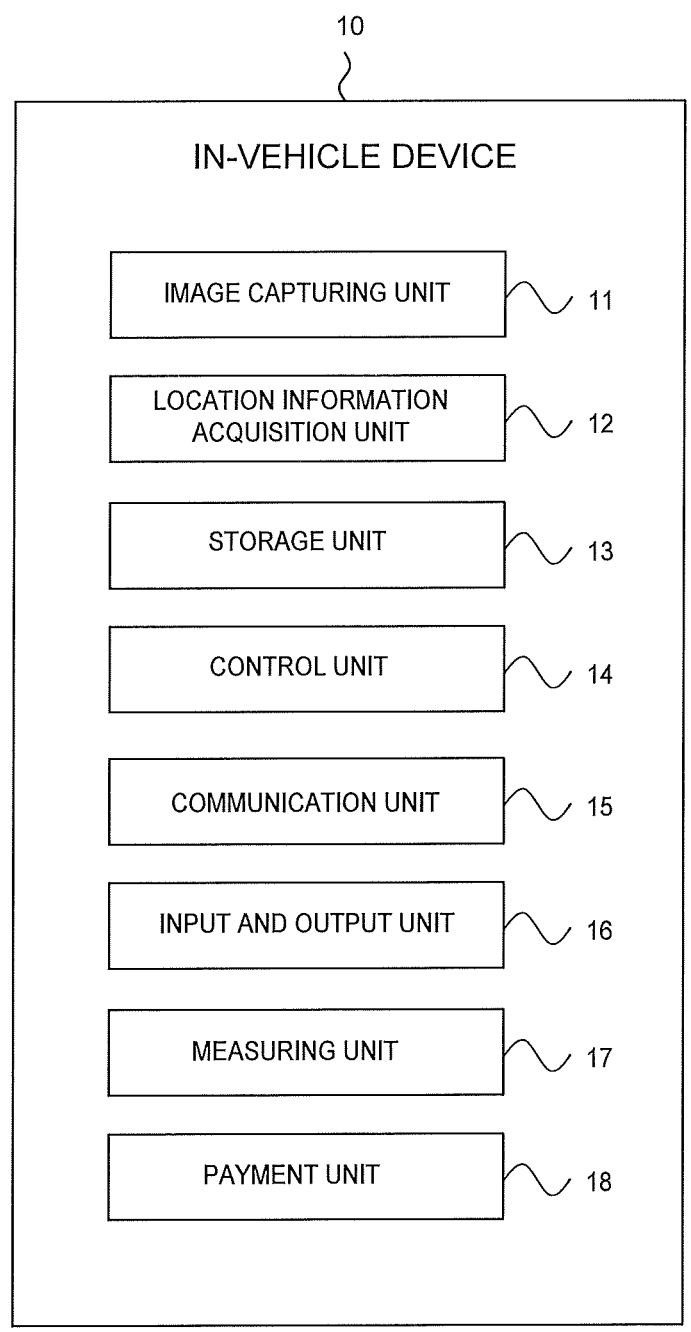
FIG. 2A is a functional block diagram illustrating an in-vehicle device of the present embodiment.

As illustrated in FIG. 2A, the in-vehicle device 10 includes an image capturing unit 11, a location information acquisition unit 12, a storage unit 13, a control unit 14, a communication unit 15, an input and output unit 16, a measuring unit 17, and a payment unit 18.

The image capturing unit 11 includes a so-called in-vehicle camera to capture an image of the outside (for example, the front, the side, the rear, and the like) of the vehicle 1. The image capturing unit 11 may create a continuous video of the outside of the vehicle 1 while the vehicle 1 is traveling or being stopped, and may store the created video in the storage unit 13. As an alternative example, any communication terminal, such as a smartphone, may function as the image capturing unit 11.

The location information acquisition unit 12 includes one or more receivers corresponding to any satellite positioning system. For example, the location information acquisition unit 12 may include a global positioning system (GPS) receiver. The location information acquisition unit 12 detects location information illustrating a location at which the vehicle 1 is being stopped or traveling. The location information acquisition unit 12 may further include an electronic compass, and may obtain information on the direction in which the vehicle 1 is facing.

The storage unit 13 is a device that records or stores various kinds of information, and includes one or more memories. Here, the "memory" is, for example, a semiconductor memory, a magnetic memory, or an optic memory, but is not limited thereto. Each memory included in the storage unit 13 may function as, for example, a primary storage device, a secondary storage device, or a cache memory. The storage unit 13 stores any information related to the operation of the vehicle 1. The storage unit 13 may store information on the results analyzed or processed by the control unit 14. The storage unit 13 may store various information related to the operation or control of the vehicle 1, such as storing a vehicle control program of a subject vehicle.

The control unit 14 includes one or more processors. Here, the "processor" may be a general-purpose processor or a processor dedicated to a specific process. For example, an electronic control unit (ECU) mounted on the vehicle 1 may function as the control unit 14. The control unit 14 controls the overall operation of the vehicle 1. The control unit 14 controls the other functional units included in the in-vehicle device 10, and performs all control related to traveling or operation of the vehicle 1. For example, the control unit 14 can obtain the image from the image capturing unit 11 and analyze the obtained image to detect the subject and the behavior of the subject.

The communication unit 15 includes a communication module that performs communication between the vehicle 1 and the server 2. The communication unit 15 may include, if needed, a communication module that performs inter-vehicle communication between the vehicle 1 and another vehicle not via the server 2. The communication unit 15 may include a communication module connected to the network NW, or a communication module corresponding to a mobile communication standard, such as 4G (4th Generation) and 5G (5th Generation). For example, a data communication module (DCM) and the like mounted on the vehicle 1 may function as the communication unit 15.

The input and output unit 16 includes an input interface that detects an input of the user and sends the input information to the control unit 14. Examples of the input interface may include a touchscreen integrally provided with physical keys, capacitive keys, a panel display, or a microphone that receives an audio input. However, the input interface is not limited thereto, and may be any input unit. The input and output unit 16 includes an output interface that outputs, to the user, information generated by the control unit 14, or information read from the storage unit 13. Examples of the output interface may include a panel display that outputs information in the form of an image or video, or a speaker that outputs information in the form of audio. However, the output interface is not limited thereto, and may be any output unit. For example, the input and output unit 16 can output the content of a suggestion based on the behavior of the subject.

The measuring unit 17 includes a measuring device used by a person, and measures a value related to the person. Examples of the value may include blood pressure, body temperature, grip strength, and weight.

The payment unit 18 includes a payment terminal used in payment for goods or services sold, in the vehicle 1, and completes the payment between a seller and a customer. The payment unit 18 accepts, for example, a credit card, a debit card, a prepaid card, cash, or the like, from the customer, and completes the payment according to the payment amount. As an alternative example, the payment unit 18 may complete the payment via an application downloaded to a mobile terminal owned by the customer.

Figure 2B:
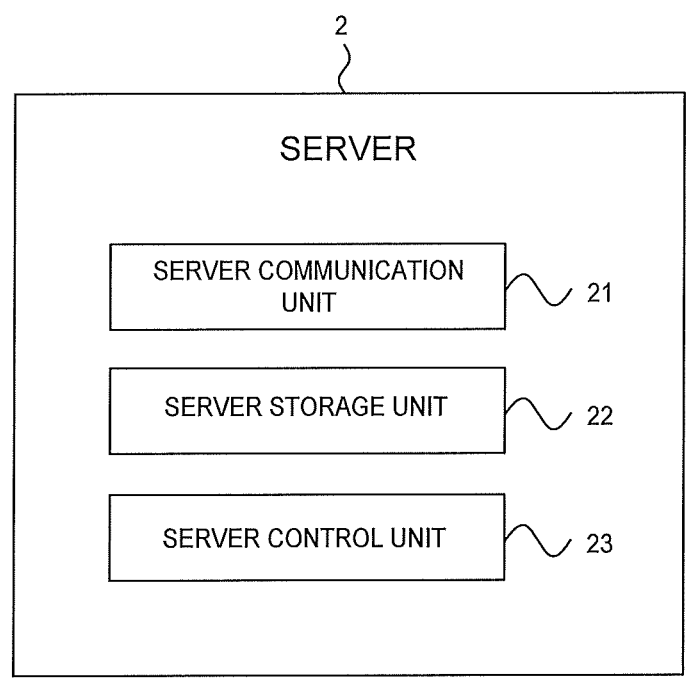
FIG. 2B is a functional block diagram illustrating a server of the present embodiment.

As illustrated in FIG. 2B, the server 2 includes a server communication unit 21, a server storage unit 22, and a server control unit 23.

The server communication unit 21 includes a communication module that performs communication between the server 2 and the vehicle 1, or between the server 2 and the user terminal 3. The server communication unit 21 may include a communication module connected to the network NW. The server communication unit 21 can obtain information output from the vehicle 1 and send the information to a terminal of a registered party concerned.

The server storage unit 22 is a device that records or stores various kinds of information, and includes one or more memories. Each memory included in the server storage unit 22 may function as, for example, a primary storage device, a secondary storage device, or a cache memory. The server storage unit 22 stores, for example, the information output from the vehicle 1. The server storage unit 22 may store various programs related to the operation or control of a server control program or the entire information processing system S.

The server control unit 23 includes one or more processors. The server control unit 23 controls the server communication unit 21 and the server storage unit 22, and performs all controls related to the overall operation of the server 2.

Figure 2C:
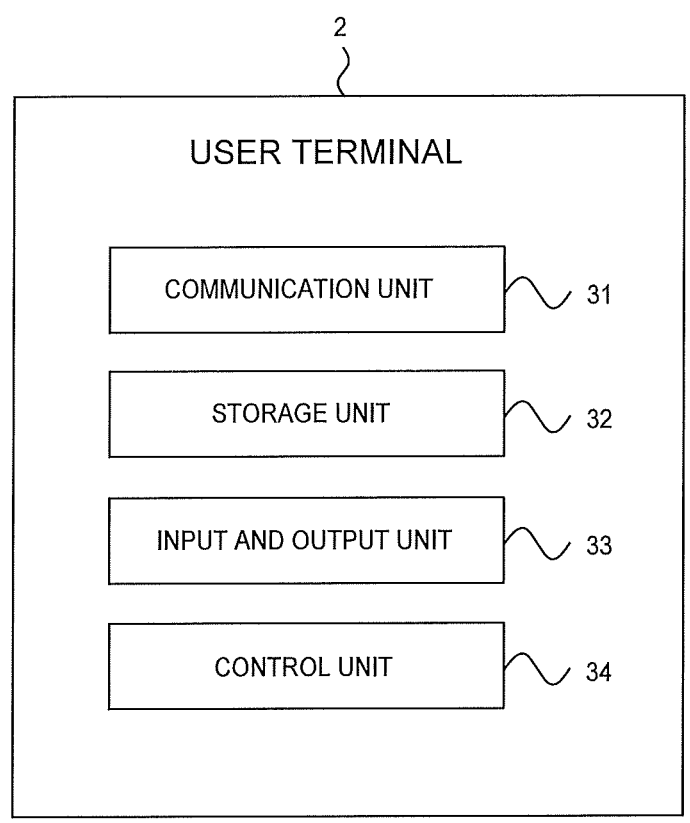
FIG. 2C is a functional block diagram illustrating a user terminal of the present embodiment.

As illustrated in FIG. 2C, the user terminal 3 includes a communication unit 31, a storage unit 32, an input and output unit 33, and a control unit 34.

Hardware configurations of the communication unit 31, the storage unit 32, the input and output unit 33, and the control unit 34 are the same as the hardware configurations of the communication unit 15, the storage unit 32, the input and output unit 16, and the control unit 14 of the in-vehicle device 10, respectively. Therefore, the descriptions will be omitted.

Figure 3:
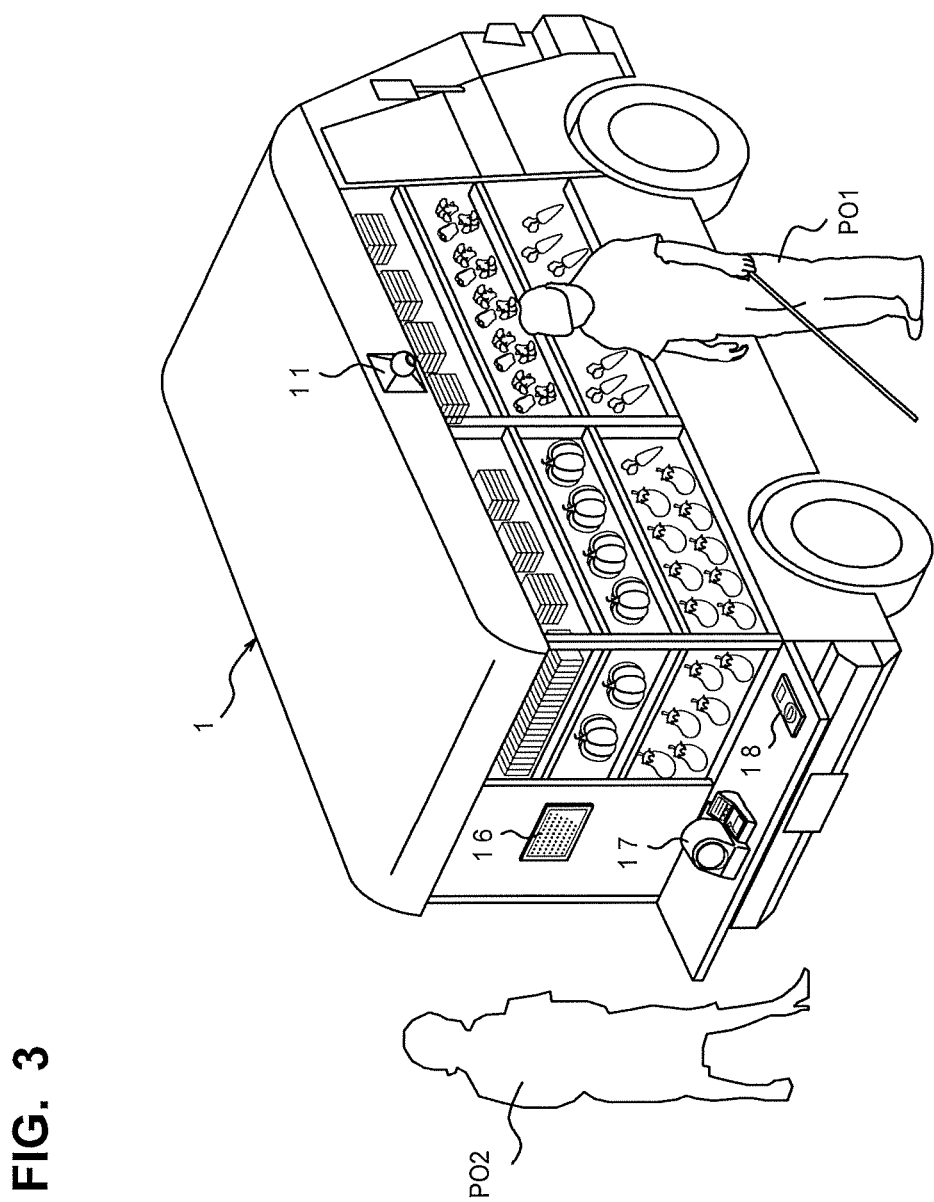
FIG. 3 is a perspective view illustrating a vehicle of the present embodiment.

A control method executed by the information processing system S will be described in detail below. The in-vehicle device 10 captures an image at any interval while the vehicle 1 is traveling or being stopped. In the present embodiment, as an example, a case where the image capturing unit 11 captures a moving image while the vehicle 1 is being stopped will be described as illustrated in FIG. 3.

The in-vehicle device 10 detects the subject from the captured image. When detecting the subject, the in-vehicle device 10 refers to a database (see FIG. 4) stored in the storage unit 13. The database illustrated in FIG. 4 stores a feature amount and address information in association with a person's ID. The feature amount may be extracted from, for example, the image obtained by previously capturing a face or the like of a subject to be detected. In the present embodiment described below, as an example, the in-vehicle device 10 receives a request for monitoring an elderly parent from the user terminal 3 of his or her family member living at a distance, and extracts the feature amount from the image of the parent received with the request and stores the feature amount in the storage unit 13. The in-vehicle device 10 also receives address information of the elderly parent from the user terminal 3 of the family member and stores the address information in the storage unit 13. However, in another embodiment, the in-vehicle device 10 may obtain the feature amount and the address information by any other method. In another embodiment, the database illustrated in FIG. 4 may store the name, the date of birth, and the like, in association with the person's ID.

The in-vehicle device 10 according to the present embodiment determines whether or not the detected subject is a person stored in the database based on a comparison between the feature amount previously stored in the storage unit 13 and the feature amount extracted from the captured image. In the example illustrated in FIG. 3, the in-vehicle device 10 detects a person P01 and a person P02 from the captured image as a result of such a comparison.

When detecting the person P01 and the person P02, the in-vehicle device 10 recognizes behaviors of the subjects by analyzing the captured image. The in-vehicle device 10 can employ any image analysis method in the behavior recognition, for example, machine learning. In the present embodiment, the in-vehicle device 10 recognizes that the person P01 is walking with a cane and the person P02 is limping. In other embodiments, the behavior may include limping, coughing, wearing a mask, blowing his or her nose, and the like. As illustrated in FIG. 5, the in-vehicle device 10 stores a date of detection and the recognized behavior in association with the detected subject.

As illustrated FIG. 3, the in-vehicle device 10 according to the present embodiment includes the measuring unit 17 that is a blood-pressure gauge and the payment unit 18 which is the payment terminal. The in-vehicle device 10 can determine who is using the measuring unit 17 or the payment unit 18 by analyzing the captured image or by receiving user identification information input by the user. As an alternative example, the in-vehicle device 10 can determine who has purchased which item, based on the user identification information included in payment information obtained from the payment unit 18.

The in-vehicle device 10 obtains values respectively measured from the person P01 and the person P02 using the measuring unit 17, and stores the obtained values in association with the persons' IDs, respectively, as illustrated in FIG. 5. Further, the in-vehicle device 10 obtains information on an item purchased by the person P02 using the payment unit 18 and stores the information in association with the person's ID.

As illustrated in FIG. 3, the in-vehicle device 10 includes the input and output unit 16. The input and output unit 16 of the present embodiment is a display. The in-vehicle device 10 can display the content of the suggestion based on the behavior of the subject. For example, the in-vehicle device 10 suggests to the person P01 who is walking with a cane that he or she purchase a medicine. As another example, the in-vehicle device 10 suggests the person P02 who is limping that he or she receive a doctor's diagnosis.

The in-vehicle device 10 can calculate a necessity degree of sending the information associated with the subject to the terminal of the party concerned via the network NW based on the behavior of the subject. Examples of the party concerned are as described above. The in-vehicle device 10 sends the information when it is determined that the calculated necessity degree is equal to or higher than the threshold. The information may be sent by, for example, e-mail. For example, when the in-vehicle device 10 recognizes that the person P01 is walking with a cane and coughing, the in-vehicle device 10 determines that the necessity degree of sending the information is equal to or higher than the threshold, and sends the information associated with the person P01, i.e. the behavior, the measured value, the purchased item, and the like, to the user terminal 3 of the family member who has requested monitoring of the person P01. In addition, the in-vehicle device 10 may notify the user terminal 3 of the family member that it is better to bring the person P01 to the hospital.

Before sending the information associated with the subject to the terminal of the party concerned, the in-vehicle device 10 may inquire of the subject via the input and output unit 16 whether or not to send the information. When receiving a permission to send the information from the subject via the input and output unit 16, the in-vehicle device 10 sends the information.

When it is determined that at least one of the one or more designated subjects has not been detected, the in-vehicle device 10 can instruct the vehicle 1 to move to the address of the undetected subject. For example, the in-vehicle device 10 receives the designation of the person P01, the person P02, and a person P03. However, the in-vehicle device 10 has not yet detected the person P03 as illustrated in FIG. 5. Consequently, the in-vehicle device 10 can obtain the address information of the person P03 from the storage unit 13, and can instruct the vehicle 1 to move to the address. If the vehicle 1 moves to the address and the in-vehicle device 10 captures an image of the surroundings, it is highly likely that the in-vehicle device 10 can detect the person P03 from the captured image. Additionally, the in-vehicle device 10 may receive, from the terminal of the party concerned with the person P03, location information of a place where the person P03 is likely to be present. When the in-vehicle device 10 has not yet detected the person P03, the in-vehicle device 10 can instruct the vehicle 1 to move to a place where the person P03 is likely to be present.

In another embodiment, when the in-vehicle device 10 cannot detect the person P03 although the vehicle 1 has moved to the address of the person P03 or to a place where the person P03 is likely to be present, the in-vehicle device 10 can send a feature amount of the person P03 to other vehicles and request the other vehicles to cooperate to detect the person P03. The in-vehicle device 10 can receive a detection notification when the person P03 is detected by the other vehicles. With this configuration, the in-vehicle device 10 can perform a search for a person in a wider area. In another embodiment, when the person P03 cannot be detected although the vehicle 1 has moved, the in-vehicle device 10 can display on the input and output unit 16 that eyewitness information of the person P03 is being collected, while selling the goods or services. Here, the in-vehicle device 10 may display, for example, an image of a face or the name of the person P03 on the input and output unit 16. With this configuration, the in-vehicle device 10 can collect information from other customers and find the person P03 earlier. Additionally, when it is determined that the number of times the person P03 has not been detected reaches a predetermined value although the vehicle 1 has moved, or that the person P03 has not been detected for a predetermined period (for example, three months) since the person P03 was last detected, the in-vehicle device 10 may send the content of the determination to the terminal of the party concerned with the person P03. In still another embodiment, when the vehicle 1 detects the person P03 as a result of moving, the in-vehicle device 10 can compare a behavior of the person P03 when detected and a behavior of the person P03 when last detected, and detect changes in the behaviors of the person P03. When the changes indicate that the health condition has deteriorated (for example, the person P03 didn't limp when last detected but is limping now), the in-vehicle device 10 may notify the terminal of the party concerned that the person P03 has been detected and his or her health condition has deteriorated. This configuration enables the party concerned to take early measures.

Figure 6:
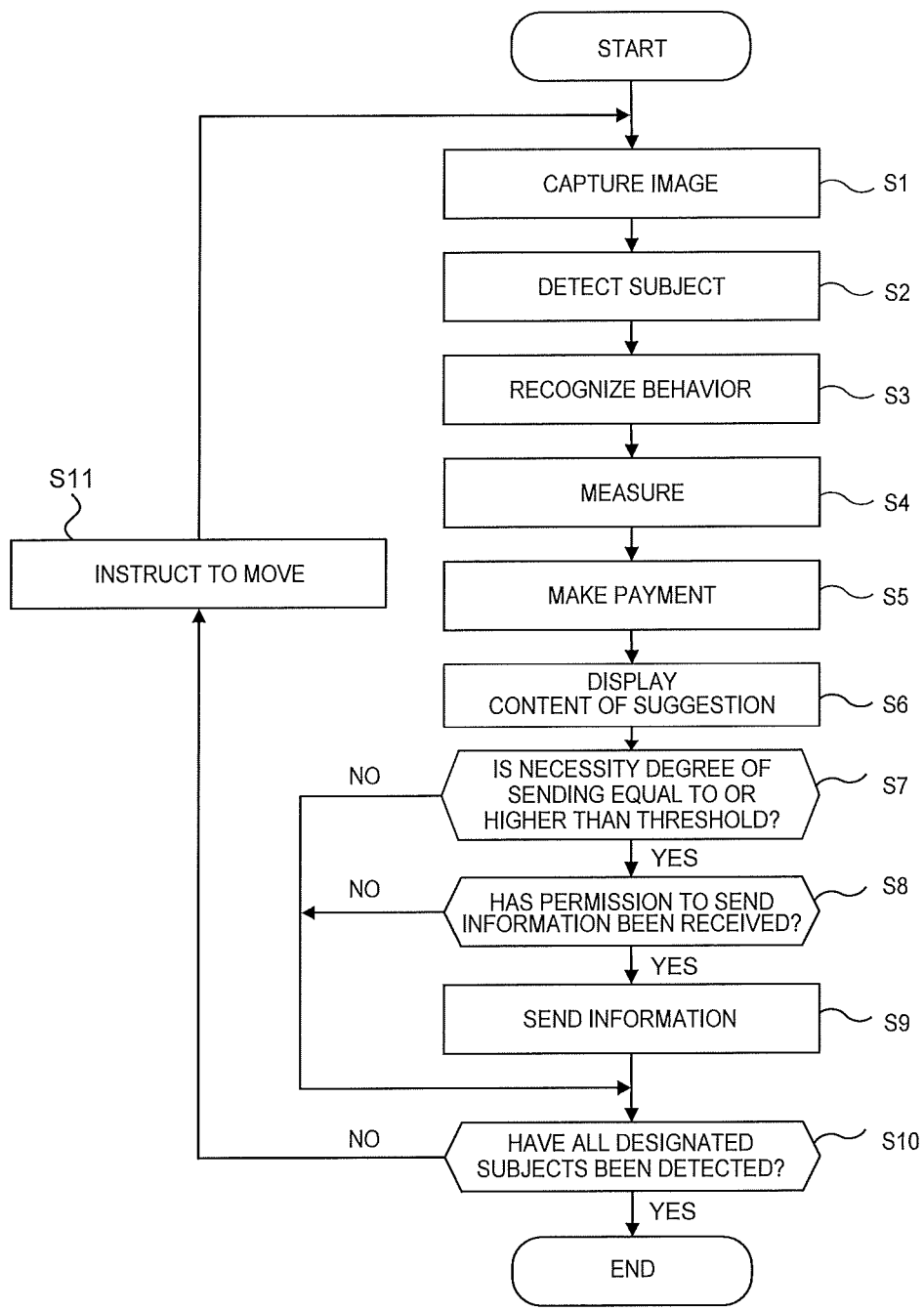
FIG. 6 is a flowchart illustrating processing executed by the in-vehicle device of the present embodiment.

FIG. 6 is a flowchart of an information processing method executed by the in-vehicle device 10 of the present embodiment at any time.

Step S1: The in-vehicle device 10 captures an image.

Step S2: The in-vehicle device 10 detects the subject from the captured image.

Step S3: The in-vehicle device 10 recognizes the behavior of the detected subject.

Step S4: The in-vehicle device 10 measures the value related to the person.

Step S5: The in-vehicle device 10 obtains information on the payment made by the subject via the payment unit 18.

Step S6: The in-vehicle device 10 displays the content of the suggestion based on the behavior of the subject.

Step S7: Based on the behavior of the subject, the in-vehicle device 10 calculates the necessity degree of sending the information associated with the subject to the terminal of the party concerned, and also determines whether the necessity degree is equal to or higher than a threshold.

Step S8: When it is determined that the necessity degree is equal to or higher than the threshold (YES in step S7), the in-vehicle device 10 determines whether the permission to send the information has been received from the subject.

Step S9: When it is determined that the permission to send the information has been received from the subject (YES in step S6), the in-vehicle device 10 sends the information.

Step S10: The in-vehicle device 10 determines whether all the designated subjects have been detected or not.

Step S11: When it is determined that at least one of all the designated subjects has not been detected (NO in step S10), the in-vehicle device 10 instructs the vehicle 1 to move.

As stated above, according to the present embodiment, the in-vehicle device 10 obtains an image captured by the image capturing unit 11, detects a subject in the obtained image based on the features stored in the storage unit 13, recognizes the behavior of the detected subject from the obtained image, and stores the detected subject and the recognized behavior in association with each other. With this configuration, the in-vehicle device 10 enables the party concerned to check the daily health condition or safety of a target (for example, an elderly person) without undue burden of operating the terminal, or the like, on the target.

Moreover, according to the present embodiment, the in-vehicle device 10 further includes the measuring unit 17 configured to be used by the person to measure the value related to the person. The control unit 14 stores the detected subject and the measured value for the subject in association with each other in the storage unit 13. With this configuration, the in-vehicle device 10 can obtain the measured value of the target without additional burden on the target in response to the target using the measuring unit 17.

Moreover, according to the present embodiment, the in-vehicle device 10 further includes the input and output unit 16. The control unit 14 causes the input and output unit 16 to output the content of the suggestion based on the behavior of the subject. With this configuration, the in-vehicle device 10 can suggest to the target improving his or her health.

Moreover, according to the present embodiment, the in-vehicle device 10 further includes the communication unit 15 configured to communicate with the terminal of the party concerned with the subject via the network NW. The control unit 14 sends information associated with the subject to the terminal of the party concerned via the communication unit 15. With this configuration, the in-vehicle device 10 can notify the information on the target (for example, blood pressure and the purchased item) to the terminal of the party concerned, and thus, for example, the party concerned can monitor the target from a distance.

Moreover, according to the present embodiment, based on the behavior of the subject, the control unit 14 calculates the necessity degree of sending the information associated with the subject to the terminal of the party concerned, and sends the information when it is determined that the necessity degree is equal to or higher than the threshold. With this configuration, the in-vehicle device 10 sends the information only when it is necessary to send, and thus the processing load can be reduced.

Moreover, according to the present embodiment, the control unit 14 receives from the subject via the input and output unit 16 the permission to send the information associated with the subject to the terminal of the party concerned, and upon receiving the permission to send the information, sends the information. With this configuration, the in-vehicle device 10 can protect the personal information of the target.

Moreover, according to the present embodiment, the storage unit 13 stores one or more subjects and addresses in association with each other. When it is determined that at least one of one or more designated subjects has not been detected, the control unit 14 instructs the vehicle 1 to move to the address of the at least one undetected subject. With this configuration, the in-vehicle device 10 can comprehensively check the daily health condition of all the designated subjects.

Moreover, according to the present embodiment, the in-vehicle device 10 further includes the payment unit 18. The control unit 14 obtains the payment information from the payment unit 18, and stores the detected subject and information on the payment made by the subject via the payment unit 18 in association with each other. With this configuration, the in-vehicle device 10 can obtain the payment information of the target without additional burden on the target in response to the target making the payment by the payment unit 18.

Moreover, according to the present embodiment, when it is determined that at least one of one or more subjects has not been detected for a predetermined period since the subject was last detected, the control unit 14 notifies the terminal of the party concerned with the undetected subject. With this configuration, for example, the control unit 14 can notify the party concerned with the target who may find it difficult to go out, and enable the party concerned to take early measures.

The present disclosure has been described above with reference to the drawings and the embodiments. However, it is to be noted that a person skilled in the art can easily make variations and modifications thereto, based on the present disclosure. Therefore, it is also to be noted that these variations and modifications fall within the scope of the present disclosure. For example, functions and the like included in each element, each step, or the like can be rearranged so as not to be logically contradictory, and a plurality of elements, steps, or the like may be combined into one or divided.

A configuration is available in which any vehicle, server, or user terminal respectively serves as the vehicle 1, the server 2, or the user terminal 3 according to the embodiment stated above. Specifically, a program, which describes the content of a process for implementing each function of the vehicle 1, the server 2, or the user terminal 3 according to the embodiment, is stored in the memory of the any vehicle, server, or user terminal, and such a program is read and executed by the processor of the any vehicle, server, or user terminal. Therefore, the disclosure according to the present embodiment can also be implemented as a program that can be executed by a processor.

What is claimed is:

1. An in-vehicle device, comprising:
a control unit;
a storage unit configured to store features of each subject that is a person; and
an image capturing unit, wherein
the control unit is configured to:
obtain an image captured by the image capturing unit;
detect a subject in the obtained image based on the features stored in the storage unit;
recognize a behavior of the detected subject from the obtained image; and
store the detected subject and the recognized behavior in association with each other,
the storage unit is configured to store one or more subjects and addresses in association with each other,
the control unit is configured to, when it is determined that at least one of one or more designated subjects has not been detected, instruct a vehicle to move to an address of at least one undetected subject, and after the vehicle moves to the address of the at least one undetected subject, the control unit is configured to obtain the image captured by the image capturing unit and detect the undetected subject in the obtained image.

2. The in-vehicle device according to claim 1, further comprising:
a measuring unit configured to measure a value related to a person who uses a measuring device,
wherein the control unit is configured to store the detected subject and the measured value for the subject in association with each other in the storage unit.

3. The in-vehicle device according to claim 1, further comprising:
an output unit,
wherein the control unit is configured to cause the output unit to output content of a suggestion based on the behavior of the subject.

4. The in-vehicle device according to claim 1, further comprising:
a communication unit configured to communicate with a terminal of a party concerned with the subject via a network,
wherein the control unit is configured to send information associated with the subject to the terminal of the party concerned via the communication unit.

5. The in-vehicle device according to claim 4, wherein the control unit is configured to:
calculate, based on the behavior of the subject, a necessity degree of sending the information associated with the subject to the terminal of the party concerned; and
send the information associated with the subject when it is determined that the necessity degree is equal to or higher than a threshold.

6. The in-vehicle device according to claim 5, further comprising:
an input unit,
wherein the control unit is configured to:
receive from the subject via the input unit a permission to send the information associated with the subject to the terminal of the party concerned, and;
send the information when receiving the permission to send the information.

7. The in-vehicle device according to claim 1, further comprising:
a payment unit configured to make a payment for goods or services sold, in a vehicle provided with the in-vehicle device,
wherein the control unit is configured to store the detected subject and information on the payment made by the subject via the payment unit in association with each other.

8. The in-vehicle device according to claim 7, wherein the control unit is configured to obtain information on an item purchased by the subject using the payment unit and store the information in association with the subject.

9. The in-vehicle device according to claim 1, wherein the control unit is configured to:
receive designation of two or more of the subjects;
detect one of the two or more designated subjects in the obtained image;
determine whether or not another of the two more designated subjects has been detected;
when the other of the two or more designated subjects has not been detected, instruct the vehicle to move to an address of the other of the two or more designated subjects.

10. The in-vehicle device according to claim 9, wherein the vehicle is a vehicle other than a vehicle in which the in-vehicle device is disposed.

11. A control method in an in-vehicle device including a control unit, a storage unit configured to store features of each subject that is a person, and an image capturing unit, the method comprising:
storing one or more subjects and addresses in association with each other in the storage unit;
obtaining an image captured by the image capturing unit;
detecting a subject in the obtained image based on the features stored in the storage unit;
recognizing a behavior of the detected subject from the obtained image;
storing the detected subject and the recognized behavior in association with each other;
when it is determined that at least one of one or more designated subjects has not been detected, instructing a vehicle to move to an address of at least one undetected subject; and
after the vehicle moves to the address of the at least one undetected subject, obtaining the image captured by the image capturing unit and detecting the undetected subject in the obtained image.

12. A non-transitory computer readable medium storing a program for an in-vehicle device including a control unit, a storage unit configured to store features of each subject that is a person, and an image capturing unit, the program, when executed, causing the in-vehicle device to:
store one or more subjects and addresses in association with each other in the storage unit;
obtain an image captured by the image capturing unit;
detect a subject in the obtained image based on the features stored in the storage unit;
recognize a behavior of the detected subject from the obtained image;
store the detected subject and the recognized behavior in association with each other;
when it is determined that at least one of one or more designated subjects has not been detected, instruct a vehicle to move to an address of at least one undetected subject; and
after the vehicle moves to the address of the at least one undetected subject, obtain the image captured by the image capturing unit and detect the undetected subject in the obtained image.

13. A vehicle, comprising:
a control unit;
a storage unit configured to store subjects that are one or more persons in association with features and an address for each of the subjects; and
an image capturing unit, wherein:
the control unit is configured to:
obtain an image captured by the image capturing unit;
detect a subject in the obtained image based on the features stored in the storage unit;
recognize a behavior of the detected subject from the obtained image; and
store the detected subject and the recognized behavior in association with each other;
when it is determined that at least one of one or more designated subjects has not been detected, instruct the vehicle to move to an address of at least one undetected subject; and
after the vehicle moves to the address of the at least one undetected subject, obtain the image captured by the image capturing unit and detect the undetected subject in the obtained image.

14. The vehicle according to claim 13, wherein the control unit is configured to, when it is determined that at least one of one or more subjects has not been detected for a predetermined period since the subject was last detected, notify a terminal of a party concerned with the undetected subject.

* * * * *